(12) United States Patent
Scheurer et al.

(10) Patent No.: US 8,613,705 B2
(45) Date of Patent: Dec. 24, 2013

(54) CENTRAL VENOUS PRESSURE SENSOR AND METHOD TO CONTROL A FLUID OR VOLUME OVERLOAD THERAPY

(75) Inventors: Elizabeth S. Scheurer, Minneapolis, MN (US); Ramesh Wariar, Blaine, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 605 days.

(21) Appl. No.: 12/535,390

(22) Filed: Aug. 4, 2009

(65) Prior Publication Data

US 2010/0076398 A1 Mar. 25, 2010

Related U.S. Application Data

(60) Provisional application No. 61/098,424, filed on Sep. 19, 2008.

(51) Int. Cl.
*A61B 5/02* (2006.01)

(52) U.S. Cl.
USPC ............................. 600/485; 604/9; 604/508

(58) Field of Classification Search
USPC ................... 600/483, 486, 505, 485
See application file for complete search history.

(56) References Cited

U.S. PATENT DOCUMENTS

| | | | |
|---|---|---|---|
| 5,085,213 A | 2/1992 | Cohen | |
| 6,287,516 B1 * | 9/2001 | Matson et al. | 422/44 |
| 6,497,676 B1 | 12/2002 | Childers et al. | |
| 6,623,470 B2 * | 9/2003 | Munis et al. | 600/486 |
| 6,746,398 B2 * | 6/2004 | Hervy et al. | 600/300 |
| 7,024,248 B2 | 4/2006 | Penner et al. | |
| 7,118,534 B2 | 10/2006 | Ward et al. | |
| 7,381,190 B2 | 6/2008 | Sugrue et al. | |
| 7,507,220 B2 | 3/2009 | Childers et al. | |
| 2004/0019285 A1 * | 1/2004 | Eigler et al. | 600/488 |

(Continued)

FOREIGN PATENT DOCUMENTS

| | | |
|---|---|---|
| JP | 2006102237 A | 4/2006 |
| JP | 2010527247 A | 8/2010 |
| WO | 0123277 A1 | 4/2001 |
| WO | WO2008055248 A2 | 8/2008 |

OTHER PUBLICATIONS

Labato, M.A., "Peritoneal Dialysis in Emergency and Critical Care Medicine", Clinical techniques in Small Animal Practice, vol. 15, No. 3, Aug. 1, 2000, pp. 126-135.

(Continued)

*Primary Examiner* — Patricia Mallari
*Assistant Examiner* — Vasuda Ramachandran
(74) *Attorney, Agent, or Firm* — Faegre Baker Daniels LLP

(57) ABSTRACT

An implantable system for monitoring a hydration state of a patient and adjusting fluid removal from the patient includes a pressure sensor implantable within an inferior vena cava of the patient and a processor. The pressure sensor senses and generates an output representative of a baseline inferior vena caval pressure value of the patient and chronically senses and generates outputs representative of an inferior vena caval pressure value of the patient. The processor compares differences between the baseline inferior vena caval pressure value and subsequent inferior vena caval pressure values. The processor can reside in another implantable device or in an external device/system.

13 Claims, 3 Drawing Sheets

(56) References Cited

U.S. PATENT DOCUMENTS

| | | |
|---|---|---|
| 2004/0172080 A1* | 9/2004 | Stadler et al. .................... 607/17 |
| 2005/0154320 A1* | 7/2005 | Froelich et al. ............... 600/486 |
| 2006/0009818 A1 | 1/2006 | Von Arx et al. |
| 2006/0122522 A1 | 6/2006 | Chavan et al. |
| 2007/0213599 A1 | 9/2007 | Siejko et al. |
| 2007/0255112 A1 | 11/2007 | Taepke, II et al. |
| 2008/0034836 A1 | 2/2008 | Eigler et al. |
| 2008/0071178 A1 | 3/2008 | Greenland et al. |
| 2009/0105799 A1 | 4/2009 | Hekmat et al. |

OTHER PUBLICATIONS

Reed, Kathryn L., et al., "Umbilical Venous Doppler Velocity Pulsations and Inferior Vena Cava Pressure Elevations in Fetal Lambs", Obstetrics and Gynecology, vol. 87, No. 4, pp. 617-620, 1996.

Seraj, Mohamed A. et al., "Are Heat Stroke Patients Fluid Depleted? Importance of Monitoring Central Venous Pressure as a Simple Guideline for Fluid Therapy", Resuscitation, vol. 21, No. 1, Feb. 1, 1991, pp. 33-39.

International Search Report and Written Opinion issued in PCT/US2009/052697, mailed Oct. 16, 2009, 14 pages.

\* cited by examiner

CENTRAL VENOUS PRESSURE SENSOR AND METHOD TO CONTROL A FLUID OR VOLUME OVERLOAD THERAPY

CROSS-REFERENCE TO RELATED APPLICATION

This application claims the benefit under 35 U.S.C §119 of U.S. Provisional Application No. 61/098,424, filed on Sep. 19, 2008, entitled Central Venous Pressure Sensor and Method to Control a Fluid or Volume Overload Therapy," which is herein incorporated by reference in its entirety.

TECHNICAL FIELD

The present invention relates to the field of fluid or volume overload therapies. In particular, the present invention relates to measuring a central venous pressure value of a patient to monitor and control fluid and volume overload therapies, such as renal replacement or heart failure therapies.

BACKGROUND

Healthy kidneys function to retain the correct amount or volume of fluid in the body. For a patient with chronic kidney disease, the fluid volume in the body fluctuates between overhydration and underhydration due to the inability of the kidneys to properly regulate the amount of fluid in the body. Many patients with chronic kidney disease are treated with concomitant fluid or volume overload therapies such as renal replacement therapy (RRT), pharmacological therapy (e.g. diuretic), ultrafiltration and neurotherapy. Examples of RRT include dialysis, hemofiltration, hemodiafiltration, ultrafiltration, etc., which aid in regulating the fluid volume in the patient. In many RRTs, fluid removal goals are adjusted based on the difference between the weight of the patient at the beginning of the RRT and his/her "dry weight" or "normal hydration state". However, traditional methods used to determine the dry weight or the normal hydration state of a patient, such as body weight, blood pressure, and clinical status, can be inaccurate. Because patients with renal disease often experience weight loss as a part of the renal disease state, the dry weight of a patient is often overestimated, causing the patient to become overhydrated while on RRT. Overhydration can have severe cardiovascular effects such as hypertension, right heart failure, pulmonary edema and left ventricular hypertrophy. In a patient whose dry weight is underestimated, intradialytic hypotension is a common and difficult clinical management problem. There is a continuing need for improved measurement of the fluid status of a patient that can be chronically obtained before, during and after a RRT in a minimally invasive manner.

SUMMARY

In one aspect, the present invention is a method of determining a hydration state of a patient. The method includes measuring a first inferior vena caval pressure value of the patient using a pressure sensor chronically implanted at least partially within a central venous system of the patient, chronically measuring a plurality of second inferior vena caval pressure values of the patient at periodic intervals using the pressure sensor, remotely transmitting the first and second inferior vena caval pressure values to one or both of an external device and an implant within the patient, comparing differences in the first inferior vena caval pressure value to the second inferior vena caval pressure values, and correlating the differences between the first inferior vena caval pressure value and any one or a plurality of the second inferior vena caval pressure values to the hydration state of the patient.

In a second aspect, the present invention is a method of controlling a fluid or volume overload therapy being administered to a patient. The method includes sensing and generating an output representative of a baseline inferior vena caval pressure value of the patient before administering the fluid or volume overload therapy using a pressure sensor, chronically sensing and generating outputs representative of the inferior vena caval pressure value of the patient during the fluid or volume overload therapy, comparing differences between the output representative of the baseline inferior vena caval pressure value and the outputs representative of subsequent inferior vena caval pressure values generated during the fluid or volume overload therapy, and adjusting the volume overload therapy based on the differences between the baseline inferior vena caval pressure value and the subsequent inferior vena caval pressure values of the patient during the fluid or volume overload therapy.

In a third aspect, the present invention is an implantable system for monitoring a fluid level of a patient during a volume overload therapy. The implantable system includes a pressure sensor implantable within the central venous system of the patient and a processor. The pressure sensor senses and generates an output representative of a baseline inferior vena caval pressure value of the patient and chronically senses and generates, outputs representative of inferior vena caval pressure values of the patient. The processor compares differences between the baseline inferior vena caval pressure value and subsequent inferior vena caval pressure values.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
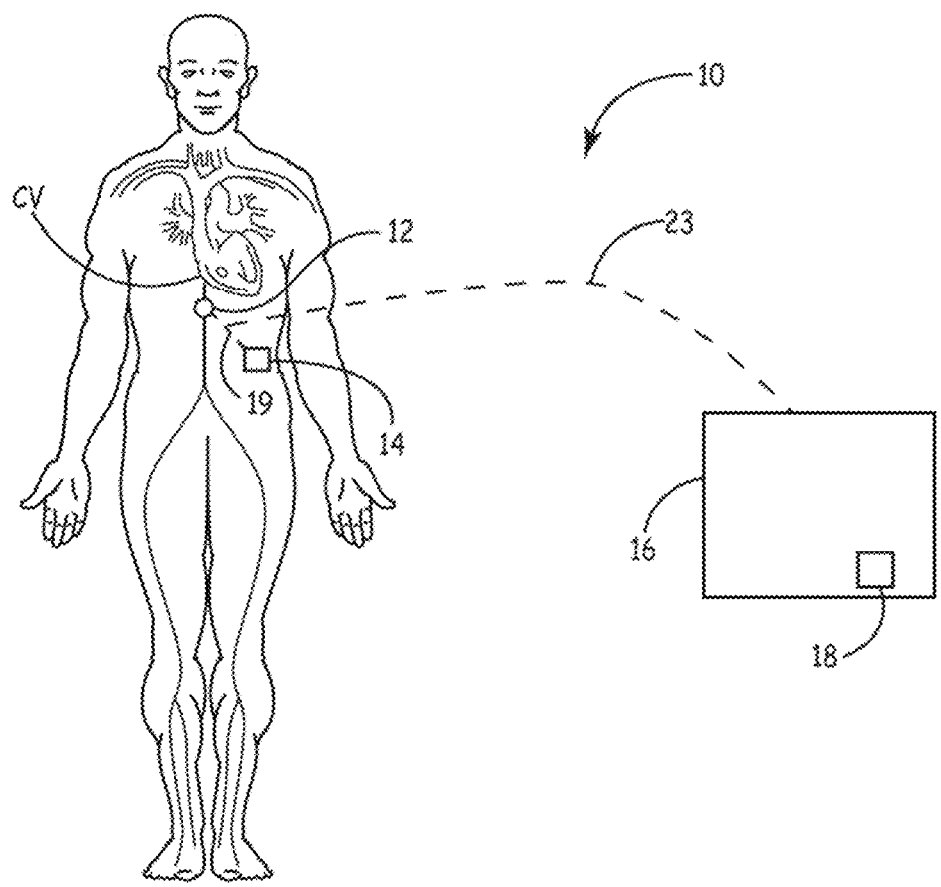
FIG. 1 is a schematic diagram of a fluid or volume overload therapy monitoring and control system according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 shows a schematic diagram of a fluid or volume overload therapy monitoring and control system 10 according to one embodiment of the present invention. As shown in FIG. 1, the fluid or volume overload therapy monitoring and control system 10 includes a pressure sensor 12, an implantable medical device ("IMD") 14 and an external device/system 16.

In the illustrated embodiment, the pressure sensor 12 and the IMD 14 are both implanted within the patient for facilitating chronic assessment of a hydration level or fluid volume of the patient during a fluid or volume overload therapy. As shown, the pressure sensor 12 is implanted within the patient's inferior vena cava with the IMD 14 implanted subcutaneously at a location remote from the pressure sensor 12. As further shown, the external device/system 16 is located external to the patient. As discussed in detail below, in various embodiments, the pressure sensor 12 and the IMD 14 are in communication with one another, and one or both of the foregoing is configured to be in communication with the external device/system 16.

As explained in detail below, according to the various embodiments of the present invention, the pressure sensor 12 of the fluid or volume overload therapy monitoring and control system 10 senses and measures inferior vena caval pressure values and utilizes this pressure data to estimate patient hydration levels. Thus, by chronically measuring the inferior vena caval pressure values of the patient, the fluid or volume overload therapy monitoring and control system 10 can measure and monitor the hydration level or fluid volume of the patient. The fluid or volume overload therapy being administered to the patient can then be adjusted based on noted trends associated with the inferior vena caval pressure values. Examples of fluid or volume overload therapies include, but are not limited to: renal replacement therapy (RRT), pharmacological therapy (e.g. diuretic), ultrafiltration and neural-therapy. Examples of renal replacement therapies include, for example: dialysis, ultrafiltration, hemofiltration, and hemodiafiltration. In addition, the fluid or volume overload therapy monitoring and control system 10 provides a minimally invasive means for chronically monitoring the hydration state of the patient.

The pressure sensor 12 can be percutaneously, or if necessary via a cut-down procedure, introduced into the inferior vena cava of the patient through any vein connected to the inferior vena cava, such as, but not limited: to the femoral vein, jugular vein, bracheocephalic vein or subclavian vein. The pressure sensor 12 can be introduced into the central venous system by any means known in the art, for example, by using a catheter delivery system. The pressure sensor 12 may be in the form of a capsule and is anchored in the inferior vena cava using an anchoring means. In one embodiment, the anchor may also provide information by, for example, measuring changes in the vascular bed. The changes could be quantified by capturing movement, such as expansion or contraction of the inferior vena cava as the fluid status of the patient fluctuates with the fluid or volume overload therapies. In another embodiment, the anchor may also have a fixed array of flow meters that are capable of capturing volume movement between a first point and a second point within the inferior vena cava. Exemplary flow meters include, but are not limited to: piezoresistive, optical or electromechanical sensors. The data captured can then be relayed to the pressure sensor 12 or used in conjunction with the data gathered by the pressure sensor 12 to monitor the hydration state of the patient. Any anchoring means known in the art may be used. In one embodiment, the pressure sensor 12 is coupled to a stent-like anchoring structure which may be self-expandable or balloon expandable, and thus can be delivered to the target implantation site using devices and techniques similar to those used to deploy coronary arterial or peripheral vascular stents. In one embodiment, the pressure sensor 12 is coupled to an anchoring structure such as those described in co-pending and commonly assigned U.S. patent application Ser. No. 11/855,725 to Greenland, et al., which is incorporated herein by reference.

In one embodiment, the pressure sensor 12 may be incorporated with a filter, such as a Greenfield filter, configured to be implanted in the inferior vena cava. Such filters are well known in the art, and are thus not described in detail herein. In one such embodiment, the pressure sensor 12 may advantageously be positioned at the top (i.e., downstream side) of the filter so that any signals from the pressure sensor 12 are not obstructed.

Still other configurations for deploying and anchoring the pressure sensor 12 to the target implantation site within the inferior vena cava (or other locations within the central venous system) will become apparent to those skilled in the art based on the foregoing.

In one embodiment, to obtain the most accurate reading, the pressure sensor 12 is positioned below the heart and above the kidneys of the patient. Although the pressure sensor 12 is discussed as being located in the inferior vena cava of the patient and measuring the inferior vena caval pressure values, it is envisioned that the superior vena caval pressure or the pulmonary artery pressure may also be measured in lieu of the inferior vena caval pressure.

The pressure sensor 12 chronically measures the central venous pressure values of the patient in order to accurately measure the dry weight of the patient. In patients with chronic kidney disease, cachexia, which leads to a decrease in lean body mass, is often present. If the normal hydration state of the patient is not accurately determined, the decrease in lean body mass may be inadvertently accounted for by fluid volume, leading to fluid overload in the patient, which in turn can lead to cardiovascular complications.

In various embodiments, the inferior vena caval pressure values are sensed before, during and after administration of the fluid or volume overload therapy. In one embodiment, the pressure sensor 12 gathers inferior vena caval pressure data between about every 3 hours and about every 5 hours, and particularly about every 4 hours. While the fluid or volume overload therapy is being administered, the pressure sensor 12 can be programmed to either gather data at shorter intervals or optionally on an "on-demand" basis in which the physician or clinician can request a real-time reading from the pressure sensor 12.

The pressure sensor 12 can have any structure and configuration providing the desired functionality. As will be appreciated, the pressure sensor 12 is configured to generate an output (i.e., current or voltage) that is proportional to the sensed inferior vena caval pressure value, and to transmit the output signal to the IMD 14 and/or the external device/system 16. In one embodiment, a programming feature may exclude or bypass the IMD 14 such that the pressure sensor 12 communicates directly with the external device/system 16. In various embodiments, the pressure sensor 12 includes one or more transducers configured to sense and generate a signal indicative of pressure within the patient's central venous. In various embodiments, the pressure transducer can be a micro-electrical-mechanical system (MEMS) device, which as will be appreciated, utilizes semiconductor techniques to build microscopic mechanical structures in a substrate made from silicon or similar materials suitable for semiconduction e.g., Graphene. In various embodiments, the pressure transducer can include a micro-machined capacitive or piezoresistive transducer exposed to the inferior vena caval pressure value. Other pressure transducer technologies, such as resistive strain gages, are known in the art and can also be employed as a pressure transducer for use in the pressure sensor 12.

As will be appreciated, the pressure sensor 12 includes various circuitry and other components to facilitate the functional aspects of the pressure sensor 12. For example, the pressure sensor 12 includes telemetry components to facilitate communication between the pressure sensor 12 and the IMD 14 and/or the external device/system 16. In various embodiments, the pressure sensor 12 may include a battery to supply operating power for the sensor components. In various other embodiments, the pressure sensor 12 may be powered from an external source. For example, in one embodiment, the pressure sensor 12 includes an acoustic transducer configured to generate an output voltage in response to acoustic energy received from another device (e.g., the IMD 14 and/or the external device/system 16). As will be appreciated, the transducer output may then be utilized to charge one or more capacitors, which are discharged to provide operating power for the other, active components of the sensor. In various other embodiments, the pressure sensor 12 may be powered by an alternative energy source, e.g., inductive or radio-frequency electromagnetic energy.

The IMD 14 can be any implantable medical device, whether now known or later developed, configured for providing the desired functionality as discussed herein. In various embodiments, the IMD 14 includes internal processing components, e.g., a processor such as a central processing unit or integrated circuit, for processing signals from the pressure sensor 12 as well as other sensors implanted in the patient as explained below. Additionally, as will be appreciated, the IMD 14 includes, in various embodiments, memory, a power supply, telemetry systems, and/or other functional components necessary to provide the desired functionality. In one embodiment, the IMD 14 is a cardiac rhythm management ("CRM") device such as a pacemaker, an implantable cardioverting defibrillator ("ICD"), or cardiac resynchronization therapy ("CRT") device (which may or may not include defibrillation capabilities). In general, pacemakers, ICDs, and CRT devices are well known in the art, and need not be described in further detail herein.

Of course, the IMD 14 need not be a CRM device. In one embodiment, for example, the IMD 14 is a drug delivery system. In various embodiments, the IMD 14 is a monitoring device only, i.e., it does not itself provide any therapeutic stimuli.

In one embodiment, the IMD 14 operates as an implantable monitor/repeater device, and thus includes a processor that receives the pressure sensor 12 output, and manipulates and processes the sensor output as described herein. For example, the processor in the IMD 14 could generate trends, waveforms, and the like, which are then transmitted to the external device/system 16. In one embodiment, the IMD 14 is operable as a data storage and transmission device, whereby the IMD 14 stores the raw pressure sensor output data and transmits it to the external device/system 16 as desired. In one embodiment, the IMD 14 is a CRM device that receives the output signal from the pressure sensor 12, which represents the sensed inferior vena caval pressure data, and uses this pressure data in a closed-loop manner to adaptively adjust therapy parameters. The foregoing therapeutic functionality can be provided in addition to or in lieu of the monitoring and/or data storage functions discussed above.

In the illustrated embodiment, the IMD 14 is operatively coupled to the pressure sensor 12 via a communication link 19. The IMD 14 is configured to receive and process the output signal(s) from the pressure sensor 12.

In one embodiment, the IMD 14 is configured to receive the output signal(s) from the pressure sensor 12 and measure a baseline inferior vena caval pressure value therefrom. In various embodiments, the baseline pressure measurement is determined by the first pressure sensor 12 according to a pre-determined regimen (i.e., daily, hourly, semi-weekly, etc.) before administration of the fluid or volume overload therapy in order to establish the patient's normal hydration state or dry weight. In one embodiment, the baseline pressure measurement is taken at least daily. In various embodiments, to enhance the accuracy of the baseline inferior vena caval pressure measurement, it is determined based on multiple or continuous readings sensed and recorded over a period of time. For example, in one embodiment, the inferior vena caval pressure value is taken substantially continuously for a pre-determined time period so as to generate a pressure data curve, which data can then be manipulated in a variety of ways to determine an accurate representative baseline inferior vena caval pressure value and the normal hydration state of the patient. In another embodiment, multiple pressure measurements are performed at pre-determined sampling rates, and the results averaged to define the baseline inferior vena caval pressure value. Still other schemes for obtaining the baseline inferior vena caval pressure value will become apparent to those skilled in the art based on the foregoing.

The IMD 14 can also be configured to obtain atmospheric or ambient (i.e. barometric) pressure data from another source and calibrate or correct the measured inferior vena caval pressure values for changes in barometric pressure.

In addition, the IMD 14 may be programmed to account for factors that may effect the central venous pressure, such as blood volume and compliance of the venous system. In one embodiment, from a waveform of about two respiration cycles, central venous pressure parameters such as mean pressure are measured and transmitted to the IMD 14 where it is stored. The measurements can then be trended and viewed by the clinician. In addition to using the trends to determine the baseline pressure measurement and the estimated dry weight of the patient, the trends are also used to set the fluid or volume overload therapy, such as by setting dialysis fluid removal goals and profiles.

The IMD 14 and the pressure sensor 12 can be in communication with each other using such means such as acoustic, RF, or optical methods, for example. Alternatively, the IMD 14 can have a wired connection to the pressure sensor 12.

In the illustrated embodiment, the IMD 14 in turn is in communication with the external device/system 16 via a communication link 23. In various embodiments, the external device/system operates to allow a physician or other caregiver to communicate with the IMD 14 and the pressure sensor 12. In various embodiments, the external device/system 16 can, itself, determine an optimal fluid or volume overload therapy based on the trends of the inferior vena caval pressure readings and the differences between the baseline inferior vena caval pressure and subsequent inferior vena caval pressures.

The trends of the inferior vena caval pressure readings and the differences between the baseline inferior vena caval pressure value and subsequent inferior vena caval pressure values can also be used while the fluid or volume overload therapy is being administered to accordingly adjust the treatment. To determine whether and how the fluid or volume overload therapy should be adjusted, a pre-volume fluid or overload therapy inferior vena caval pressure value, or baseline inferior vena caval pressure value, is first established by trending a plurality of inferior vena caval pressure values gathered before the fluid or volume overload therapy is administered. Because the pressure sensor 12 continuously measures the inferior vena caval pressure values of the patient at periodic intervals, the data is already available. As mentioned above, the baseline inferior vena caval pressure value is set as the goal during fluid or volume overload therapy. During the fluid or volume overload therapy, the trends in pressure within the inferior vena cava are compared to the baseline inferior vena caval pressure values and the fluid or volume overload therapy is accordingly adjusted. In one embodiment, adjusting the fluid or volume overload therapy includes either reducing or increasing the rate of fluid removal from the patient. For example, if the inferior vena caval pressure value is higher than the baseline inferior vena caval pressure value, greater ultrafiltration goals are used to bring the patient back to a euvolemic state.

The specific form and functionality of the external device/system 16 is not limited to any particular type of device or system. In one embodiment, the external device/system 16 includes an external programmer, monitor, or combinations thereof. For example, in one embodiment, the external device/system 16 is an external, hand-held programmer utilized by the physician or other caregiver to access data, including inferior vena caval pressure data, stored in memory within the IMD 14, as well as to program operating parameters for the IMD 14 and the sensor 12. In one embodiment, the external device/system 16 is a local monitor, e.g., a bedside monitor located in the patient's residence, configured to, among other things, retrieve inferior vena caval pressure data from the IMD 14 and store such data in its own memory or transmit the data to another device or system. In one embodiment, the external device/system 16 is a wearable monitor that is worn and carried by the patient, which may be particularly advantageous for providing ambulatory inferior vena caval pressure data. In one embodiment, the external device is integrated into the dialysis console/system or other fluid removal system when the patient is receiving a non-ambulatory treatment.

In various embodiments, the external device/system 16 includes a remote patient monitoring and management system including an external device (e.g., a local monitor or repeater) coupled to the IMD 14 via the communication link 23, a network coupled to the external device, and a remote device/system coupled to the network. Such a patient management system allows a physician or other caregiver to communicate with the IMD 14 and/or the pressure sensor 12 through the remote device in a distant location (e.g., at the physician's office while the patient is at home). As will be appreciated, the patient management system may include additional memory, e.g., a patient database, and processing capabilities. One exemplary remote patient management system that can be incorporated into the external device/system 16 is the LATITUDE patient management system available from Boston Scientific Corporation.

Communication between the IMD 14 and the external device/system 16 can be accomplished through any suitable communication means. In one embodiment, the communication link 23 is an acoustic link to facilitate acoustic telemetry between the IMD 14 and the external device/system 16. Various suitable systems and techniques for communication between an implantable device such as the IMD 14 and an external device or system are disclosed in, for example, commonly assigned U.S. Patent Application Publication 2006/0009818 to Von Arx, et al., and U.S. Pat. No. 7,024,248 to Penner, et al., the disclosures of which are incorporated herein by reference in their entireties. In one embodiment, the communication link 23 is an inductive telemetry link. In one embodiment, the communication link 23 is a far-field radio-frequency (RF) telemetry link. Still other communication methods/schemes for providing data transmission and other communication between the external device/system 16 and the IMD 14 will be apparent to those skilled in the art based on the foregoing.

In various embodiments, the external device/system 16 includes a display, alarm capabilities, or other means for communicating the retrieved inferior vena caval pressure data to the patient, the physician or other caregiver, or all of the above. In the illustrated embodiment, for example, the external device/system 16 includes an indicator 18 accessible by the patient and/or physician. In one embodiment, the indicator 18 activates when the inferior vena caval pressure reaches a predetermined value. In another embodiment, the indicator 18 activates when a difference between the baseline inferior vena caval pressure value and subsequent inferior vena caval pressure values is greater than a predetermined value. The indicator 18 can be designed to notify the patient, a clinician or a physician of significant inferior vena caval pressure elevation. If the indicator 18 is designed to notify the patient, for example through a wristwatch remotely connected to the pressure sensor 12, the patient is alerted that he/she should either schedule a visit with a physician, report to an emergency room or take other preventative measures. Because the external device/system 16 is remotely connected to the IMD 14, a clinician or physician does not have to be in close proximity to the patient to be notified that the inferior vena caval pressure of the patient has elevated to a potentially dangerous level.

Alternatively, the indicator 18 may be programmed to activate only if the difference in the baseline inferior vena caval pressure value and subsequent inferior vena caval pressure values remains greater than the predetermined value for more than one or multiple readings. The external device/system 16 may be programmed to increase the number of readings taken within a certain period of time if the difference in the baseline inferior vena caval pressure value and the subsequent inferior vena caval pressure values are greater than the predetermined level. Although the indicator 18 is discussed as activating when the difference between the baseline inferior vena caval pressure value and subsequent inferior vena caval pressure value is greater than a predetermined value, other factors may also be used to determine when the indicator 18 is activated without departing from the intended scope of the present invention.

Trends in the inferior vena caval pressure in between fluid or volume overload therapy treatments can also be helpful to clinicians and physicians. For example, the trends can be used to understand a patient's compliance and adherence to a specified diet or medication regimens. Patients with chronic kidney disease are typically on a regimented diet that recommend against or prohibit ingestion of particular types of foods that may increase the inferior vena caval pressure. By examining the trends of the inferior vena caval pressure between fluid or volume overload therapy sessions, the clinician may be able to determine if a patient deviated from the diet or neglected to take his/her medication. A deviation from the regimented diet would be indicated if the inferior vena caval pressure of the patient increased by an atypical amount.

Figure 2:
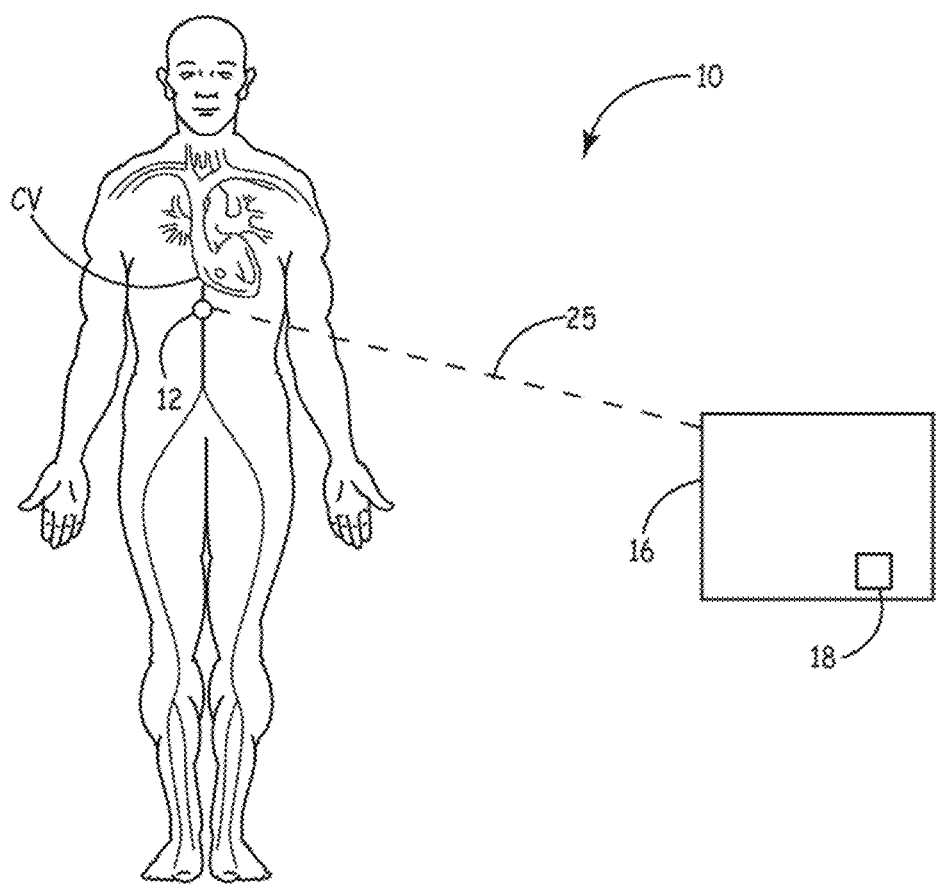
FIG. 2 is a schematic diagram of a fluid or volume overload therapy monitoring and control system according to an alternative embodiment of the present invention.

FIG. 2 is a schematic diagram of the fluid or volume overload therapy monitoring and control system 10 according to an alternative embodiment of the present invention. As shown in the embodiment of FIG. 2, the fluid or volume overload therapy monitoring and control system 10 includes a pressure sensor 12 and an external device/system 16. The pressure sensor 12 is communicably coupled to the external device/system 16 via a communication link 25. The pressure sensor 12 and the external device/system 16 can be configured in substantially the same or an identical manner to the corresponding elements of the system 10 of FIG. 1, and thus can provide the same ranges of functionality. In the embodiment of FIG. 2, however, the pressure sensor 12 does not communicate with another implanted device, i.e., the IMD 14 of the embodiment of FIG. 1. Thus, in the embodiment of FIG. 2, the outputs from the pressure sensor 12 are transmitted directly to the external device/system 16 via the communication link 25. This communication can be accomplished via any suitable means or technique, whether now known or later developed.

Figure 3:
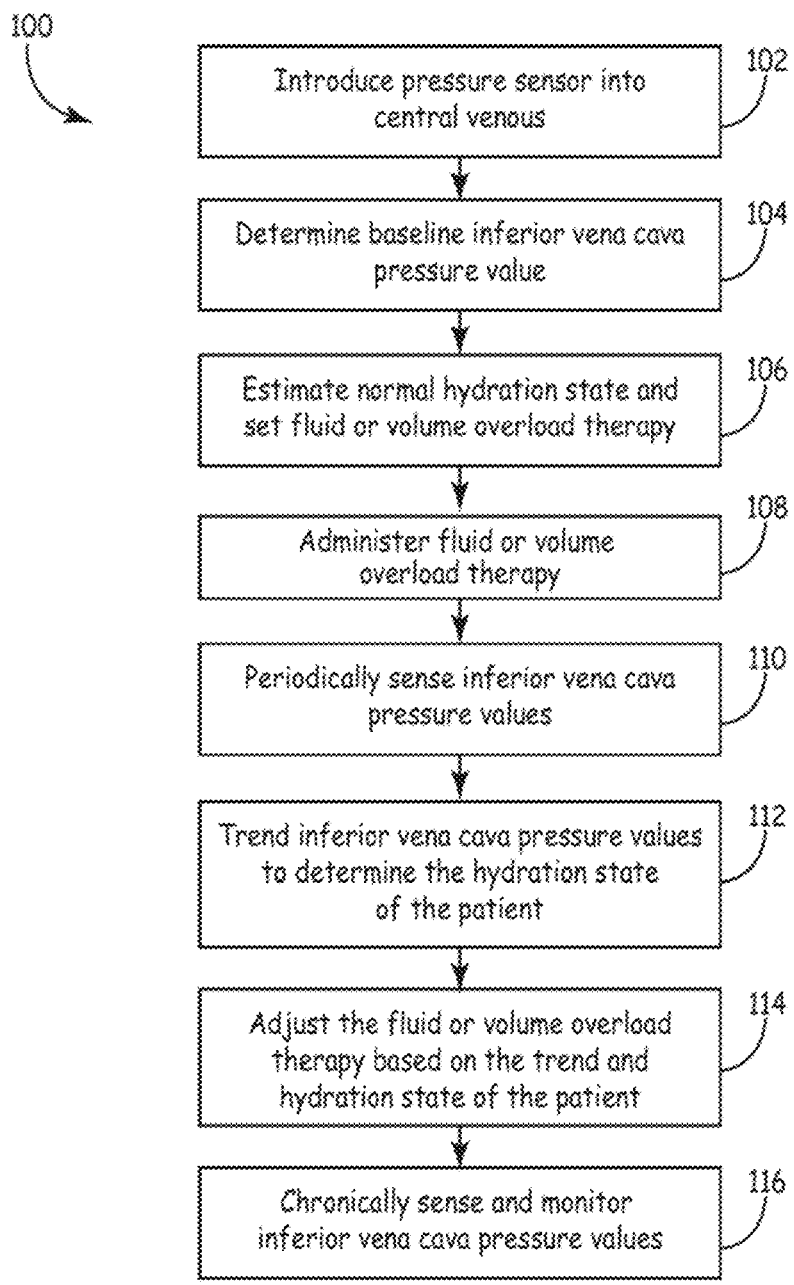
FIG. 3 is a schematic diagram of a method of monitoring and controlling a fluid or volume overload therapy according to one embodiment of the present invention.

FIG. 3 is a schematic diagram of a method 100 of monitoring a fluid or volume overload therapy by determining a hydration state or fluid level of a patient. Examples of fluid or volume overload therapies include renal replacement therapy, pharmacological therapy (e.g. diuretic), ultrafiltration and neurotherapies. The method includes first introducing a pressure sensor 12 into a circulation system of the patient and positioning the pressure sensor within the inferior vena cava of the patient. (Block 102). The pressure sensor is then anchored within an inferior vena cava of the patient. A set of initial readings of the inferior vena caval pressure are taken to determine a baseline pressure value of the inferior vena cava. (Block 104). In one embodiment, the baseline pressure value is determined based on pressure readings taken while the patient is ambulatory. Once the baseline pressure value is determined, the normal hydration state can be estimated and the proper fluid or volume overload therapy set. (Block 106). The fluid or volume overload therapy is then administered to the patient. (Block 108).

During the fluid or volume overload therapy, the pressure in the inferior vena cava is sensed at periodic intervals and communicated to a processor, which could, in various embodiments, be located within the IMD 14 and/or the external device/system 16. (Block 110). The inferior vena caval pressure values are recorded and trended to determine the hydration state of the patient at each periodic interval based on the baseline pressure value and the pressure values sensed at each periodic interval in the inferior vena cava. (Block 112). In one embodiment, the pressures are sensed or measured during the fluid or volume overload therapy while the patient is ambulatory.

The trends are based on the differences between the baseline inferior vena caval pressure value and the subsequent inferior vena caval pressure values taken during administration of the fluid or volume overload therapy. The trends may be used to determine therapy goals and profiles. The fluid or volume overload therapy may then be adjusted based on the trends and the hydration state of the patient. (Block 114). Generally, the hydration state of the patient is maintained above a minimum hydration state. However, the patient should not have too much fluid in the body. In one embodiment, the fluid or volume overload therapy is adjusted by adjusting the rate at which fluid is removed from the patient depending on the fluid or volume overload therapy goal.

Alternatively, or additionally, a clinician may be automatically notified by the external device/system 16 if predetermined conditions are detected. Thus, in various embodiments, the external device/system 16 and/or the IMD 14 are configured to automatically detect the occurrence of a rise in the inferior vena caval pressure relative to the baseline exceeding a predetermined threshold amount, so as to operate as a detection system.

For example, in various embodiments, the external device/system 16 includes a remote patient management system which in turn includes a detection and alert mechanism for notifying a clinician of significant inferior vena caval pressure increases. In one embodiment, the pressure sensor 12 is incorporated into an early detection system which is configured to generate physician alerts upon the occurrence of predetermined conditions, e.g., changes in inferior vena caval pressures exceeding a predetermined threshold amount. Exemplary automatic detection systems that can be employed in the present invention are disclosed in commonly assigned U.S. Patent Application Publication 2007/0213599 to Siejko, et. al., the disclosure of which is incorporated herein by reference in its entirety.

Even after the fluid or volume overload therapy has been administered, the fluid or volume overload therapy monitoring and control system 10 can continue to take inferior vena caval pressure readings. (Block 116). The subsequent readings may be useful to determine whether the patient is following proper protocol and to determine the normal hydration state of the patient for the next volume overload therapy session. In addition, the physician may suggest that the patient further adjust his/her lifestyle or diet based on the readings taken during the fluid or volume overload therapy.

The fluid or volume overload therapy monitoring and control system of the present invention measures the central venous pressure of a patient by percutaneously deploying a pressure sensor into the inferior vena cava of the patient. When the pressure sensor is percutaneously deployed, the process is minimally invasive and the implantation procedure is relatively fast (e.g., generally less than about an hour, and can be performed as an outpatient procedure). In addition, because the pressure sensor is percutaneously introduced into the body, the risks of infection, bleeding, subclavian stenosis, etc. also decreases. The readings are a more accurate indicator of fluid overload in the patient than those obtained by conventional methods due to the fact that they are less dependent on the pulmonary vascular bed. The method may also be used to determine fluid overload in heart failure patients as these patients may also be indicated for a vena caval filter.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of controlling a rate of fluid removal from a patient for volume overload therapy, the method comprising:
    measuring a first inferior vena caval pressure value of the patient using a pressure sensor chronically implanted at least partially within a central venous system of the patient;
    chronically measuring a plurality of second inferior vena caval pressure values of the patient at periodic intervals using the pressure sensor;
    remotely transmitting the first and second inferior vena caval pressure values to an external fluid or volume overload therapy device;
    comparing, using a processor, differences in the first inferior vena caval pressure value to the second inferior vena caval pressure values;
    correlating the differences between the first inferior vena caval pressure value and any one or a plurality of the second inferior vena caval pressure values to the hydration state of the patient; and
    adjusting a rate of fluid removal from the patient using the external fluid or volume overload therapy device based on the correlation of the differences between the first inferior vena caval pressure value and the any one or a plurality of the second inferior vena caval pressure values to the hydration state of the patient.

2. The method of claim 1, further comprising comparing trends of the first and second pressure values.

3. The method of claim 1, wherein chronically measuring the plurality of second inferior vena caval pressure values comprises chronically measuring the inferior vena caval pressure values when the patient is ambulatory.

4. The method of claim 1, wherein chronically measuring a plurality of second inferior vena caval pressure values comprises chronically measuring the inferior vena caval pressure values before, during and after adjusting the rate of fluid removal from the patient.

5. The method of claim 1, further comprising alerting a clinician when the difference between the first inferior vena caval pressure value and any one or a plurality of the second inferior vena caval pressure values exceeds a predetermined value.

6. A method of controlling a fluid or volume overload therapy being administered to a patient comprising:
   sensing and generating an output representative of a baseline inferior vena caval pressure value of the patient before administering the fluid or volume overload therapy using a pressure sensor implanted in the inferior vena cava;
   chronically sensing and generating outputs representative of the inferior vena caval pressue value of the patient during the fluid or volume overload therapy using the pressure sensor implanted in the inferior vena cava;
   transmitting a signal from the pressure sensor representative of the baseline inferior vena cava pressure and the inferior vena cava pressure value during the fluid or volume overload therapy to an external fluid or volume overload therapy device;
   comparing, using a processor, differences between the output representative of the baseline inferior vena cava pressure value and the outputs representative of subsequent inferior vena cava pressure values generated during the fluid or volume overload therapy; and
   adjusting the fluid or volume overload therapy based on the differences between the baseline inferior vena cava pressure value and the subsequent inferior vena cava pressure values of the patient during the fluid or volume overload therapy;
   wherein adjusting the fluid or volume overload therapy comprises adjusting a rate of fluid removal from the patient to maintain at least a minimum hydration state in the patient.

7. The method of claim 6, further comprising chronically sensing and generating outputs representative of the inferior vena caval pressure value of the patient after the fluid or volume overload therapy.

8. The method of claim 6, further comprising transmitting a signal from the pressure sensor to an implant within the patient.

9. The method of claim 6, further comprising determining a minimum hydration state of the patient.

10. The method of claim 6, wherein comparing the differences between the output representative of the baseline inferior vena caval pressure value and the outputs representative of the subsequent inferior vena caval pressure values of the patient during the volume overload therapy comprises determining a trend in the inferior vena caval pressure values.

11. An implantable system for monitoring a fluid level of a patient during a volume overload therapy, the implantable system comprising:
   a pressure sensor implantable within an inferior vena cava of the patient for sensing and generating an output representative of a baseline inferior vena cava pressure value of the patient and for chronically sensing and generating outputs representative of inferior vena cava pressure values of the patient;
   a processor for comparing differences between the baseline inferior vena cava pressure value and subsequent inferior vena cava pressure values of the patient to an external volume overload therapy device;
   wherein the processor is further configured to determine a rate of fluid removal from the patient based on the differences between the baseline inferior vena cava pressure value and either subsequent inferior vena cava pressure values or a target vena cava pressure value of the patient.

12. The implantable system of claim 11, wherein the processor is further configured to determine the volume overload therapy based on the differences between the baseline inferior vena caval pressure value and the subsequent inferior vena caval pressure values.

13. The implantable system of claim 11, further comprising an external system for alerting a clinician when the difference between the baseline inferior vena caval pressure value and subsequent inferior vena caval pressure values exceeds a predetermined value.

* * * * *

UNITED STATES PATENT AND TRADEMARK OFFICE
CERTIFICATE OF CORRECTION

PATENT NO.       : 8,613,705 B2
APPLICATION NO.  : 12/535390
DATED            : December 24, 2013
INVENTOR(S)      : Elizabeth S. Scheurer and Ramesh Wariar Page 1 of 1

It is certified that error appears in the above-identified patent and that said Letters Patent is hereby corrected as shown below:

In the claims
Column 11, line 28, replace "pressue" with --pressure--

Signed and Sealed this
Ninth Day of February, 2016

Michelle K. Lee
*Director of the United States Patent and Trademark Office*